United States Patent [19]

Kleemann et al.

[11] Patent Number: 5,731,350
[45] Date of Patent: Mar. 24, 1998

[54] SUBSTITUTED BENZENEDICARBOXYLIC ACID DIGUANIDES, PROCESS FOR THEIR PREPARATION, THEIR USE AS A MEDICAMENT OR DIAGNOSTIC, AND MEDICAMENT CONTAINING THEM

[75] Inventors: Heinz-Werner Kleemann, Bischofsheim; Joachim Brendel, Bad Vilbel; Jan-Robert Schwark, Frankfurt; Andreas Weichert, Egelsbach; Hans Jochen Lang, Hofheim; Udo Albus, Florstadt; Wolfgang Scholz, Eschborn, all of Germany

[73] Assignee: Hoechst Aktiengesellschaft, Frankfurt am Main, Germany

[21] Appl. No.: 747,004

[22] Filed: Nov. 7, 1996

[30] Foreign Application Priority Data

Nov. 20, 1995 [DE] Germany .................. 195 43 194.4
Jul. 1, 1996 [DE] Germany .................. 196 26 327.1

[51] Int. Cl.$^6$ .................. A61K 31/16; C07C 233/67
[52] U.S. Cl. .................. 514/616; 564/157; 564/156
[58] Field of Search .................. 514/616; 564/156, 564/157

[56] References Cited

U.S. PATENT DOCUMENTS

| | | | |
|---|---|---|---|
| 3,780,027 | 12/1973 | Cargoe et al. | 514/331 |
| 5,091,394 | 2/1992 | Englert et al. | 514/331 |
| 5,140,039 | 8/1992 | DeBernardis et al. | 514/422 |
| 5,185,364 | 2/1993 | DeBernardis et al. | 514/444 |
| 5,292,755 | 3/1994 | Englert et al. | 514/331 |
| 5,364,868 | 11/1994 | Englert et al. | 514/331 |
| 5,373,024 | 12/1994 | Lang et al. | 514/226.5 |
| 5,395,826 | 3/1995 | Naumann et al. | 514/107 |
| 5,416,094 | 5/1995 | Lal et al. | 514/307 |
| 5,498,617 | 3/1996 | Naumann et al. | 514/315 |
| 5,516,805 | 5/1996 | Lang et al. | 514/620 |
| 5,547,953 | 8/1996 | Weichert et al. | 514/603 |
| 5,559,153 | 9/1996 | Schwark et al. | 514/617 |
| 5,567,734 | 10/1996 | Schwark et al. | 514/617 |
| 5,571,842 | 11/1996 | Kleemann et al. | 514/618 |
| 5,591,754 | 1/1997 | Lang et al. | 514/603 |

FOREIGN PATENT DOCUMENTS

| | | |
|---|---|---|
| 3301493 | 8/1993 | Australia. |
| 5271693 | 12/1993 | Australia. |
| 4163593 | 1/1994 | Australia. |
| 5527994 | 2/1994 | Australia. |
| 5236893 | 6/1994 | Australia. |
| 5249093 | 6/1994 | Australia. |
| 5522994 | 8/1994 | Australia. |
| 6454494 | 8/1994 | Australia. |
| 6454394 | 12/1994 | Australia. |
| 4221896 | 2/1995 | Australia. |
| 6881194 | 2/1995 | Australia. |
| 6884494 | 2/1995 | Australia. |
| 7150794 | 3/1995 | Australia. |
| 1635495 | 10/1995 | Australia. |
| 1786195 | 11/1995 | Australia. |
| 2330095 | 1/1996 | Australia. |
| 3050495 | 3/1996 | Australia. |
| 3050595 | 3/1996 | Australia. |
| 3050695 | 3/1996 | Australia. |
| 3900895 | 5/1996 | Australia. |
| 2168315 | 1/1996 | Canada. |
| 0325964 | 8/1989 | European Pat. Off.. |
| 9426709 | 11/1994 | WIPO. |
| 9604241 | 2/1996 | WIPO. |

OTHER PUBLICATIONS

Jubian et al, "Molecular Recognition and Catalysis: Acceleration of Phosphodiester Change by Simple Hydrogen–Bonding Receptor", Chem. Abs. No. 116: 59449, (1992).
Dixon, Robert P. et al., *J. Am Chem Soc.* (1992) 114 (1), 365–6.
Duff, Henry J. et al., *Circulation*, 79(6), 1257–63 (1989).
*Eur. Heart of J.* 9 (suppl. 1):25 and 167 (1988) book of abstracts.
Schmid, Andreas et al. *Biochemical and Biophysical Research Comm.* 112–117 (1992).
Scholz, Wolfgang et al. *Cardiovascular Res.* (1995) 29(2):260–8.
Rosskopf, Dieter et al. *Cellular Physiology Biochem* (1995), (5)4, 269–275.
Scholz, Wolfgang et al. *Basic Research Cardiology* (1993) 88(5), 443–55.
Sack, Stefan et al. *J. Cardiovasc. Pharmacol.* (1994)23(1), 72–78.
Kranzhofer, Roger et al. *Circ. Res.* (1993), 73(2), 264–8.
Scholz, Wolfgang et al. *Br. J. Pharmacol.* (1993), 109(2), 562–8.
Scholz, Wolfgang et al. *J. Mol. Cell. Cardiol.* (1992) 24(7), 731–39.
Scholz, Wolfgang et al. *Cardiovascular Research.* (Feb. 1995) vol. 29(2), 184–8.
*Biological Chemistry* Hoppe–Seyler (1991), vol. 372, No. 9, p. 750.
Mitsuka, Masayuki et al. *Circulation Research* (1993), vol. 73(2):269–275.

*Primary Examiner*—Deborah Lambkin
*Attorney, Agent, or Firm*—Finnegan, Henderson, Farabow, Garrett & Dunner, L.L.P.

[57] ABSTRACT

Benzenedicarboxylic acid diguanides of the formula I

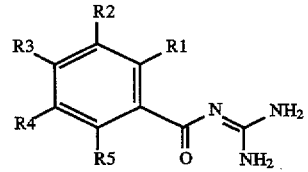

in which R(1) to R(5) have the meanings given in the claims, are useful antiarrhythmic pharmaceuticals having a cardioprotective component, even for the prevention of ischemically induced damage, in particular in the induction of ischemically induced cardiac arrhythmias. As a result of inhibition of the cellular $Na^+/H^+$ exchange mechanism, they are used for the treatment of acute or chronic damage caused by ischemia. Moreover, they are distinguished by potent inhibitory action on the proliferation of cells. They are suitable for preventing the genesis of high blood pressure.

20 Claims, No Drawings

SUBSTITUTED BENZENEDICARBOXYLIC ACID DIGUANIDES, PROCESS FOR THEIR PREPARATION, THEIR USE AS A MEDICAMENT OR DIAGNOSTIC, AND MEDICAMENT CONTAINING THEM

BACKGROUND OF THE INVENTION

The invention relates to benzenedicarboxylic acid diguanides of the formula I

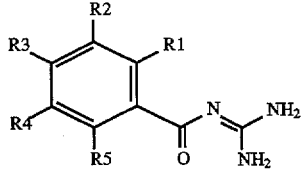

in which:
one of the radicals R(1), R(2), R(3) and R(5) is

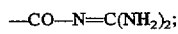

and the other radicals R(1), R(2), R(3) and R(5) in each case are:

R(1) and R(5) independently of one another are hydrogen, alkyl having 1, 2, 3 or 4 carbon atoms, F, Cl, —OR(32), —NR(33)R(34) or CF3;

R(32), R(33) and R(34) independently of one another are hydrogen or alkyl having 1, 2, 3 or 4 carbon atoms;

R(2) is hydrogen, F, Cl, Br, I, OH, —CN, $CF_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is unsubstituted or substituted by 1–3 substituents selected from the group consisting of F and Cl, —CF$_3$, methyl, methoxy and —NR(15)R(16);

R(15) and R(16) are hydrogen or —CH$_3$;

or

R(2) is R(22)—SO$_2$—, R(23)R(24)N—CO—, R(28)—CO— or R(29)R(30)N—SO$_2$—;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which a CH$_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino;

or

R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);

m is 1 or 2;

R(14) —is —(C$_3$–C$_8$)-cycloalkyl or phenyl, which is unsubstituted or substituted by 1–3 substituents selected from the group consisting of F and Cl, —CF$_3$, methyl, methoxy and —NR(15)R(16);

R(15) and R(16) are hydrogen or —CH$_3$;

or

R(4) is phenyl, which is substituted by 2, 3, 4 or five substituents selected from the group consisting of F, Cl, CF$_3$, methyl, methoxy and —NR(15)R(16);

R(15) and R(16) independently of one another are hydrogen or CH$_3$;

and their pharmaceutically tolerable salts.

Preferred compounds of the formula I are those in which:
one of the radicals R(1), R(2), R(3) and R(5) is

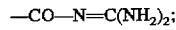

and the other radicals R(1), R(2), R(3) and R(5) in each case are

R(1) and R(5) independently of one another are hydrogen, alkyl having 1, 2, 3 or 4 carbon atoms, F, Cl, —OR(32) or —CF$_3$;

R(32) is hydrogen or alkyl having 1, 2, 3 or 4 carbon atoms;

R(2) is hydrogen, F, Cl, Br, I, OH, —CF$_3$, alkyl having 1, 2, 3 or 4 carbon atoms, alkenyl having 2, 3 or 4 carbon atoms or —(CH$_2$)$_m$R(14);

m is zero, 1 or 2;

R(14) is —(C$_3$–C$_8$)-cycloalkyl or phenyl, which is unsubstituted or substituted by 1–2 substituents selected from the group consisting of F and Cl, —CF$_3$, methyl and methoxy;

or

R(2) is R(22)—SO$_2$—, R(23)R(24)N—CO—, R(28)—CO— or R(29)R(30)N—SO$_2$—;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen, methyl or ethyl;

or

R(35) and R(36) together are 4–5 methylene groups, of which a CH$_2$ group can be replaced by oxygen, —S—, —NH— or —NCH$_3$;

R(3) is hydrogen, —SR(25), —OR(25), —NR(25)R(26) or —CR(25)R(26)R(27);

R(25) is hydrogen, alkyl having 1, 2, 3 or 4 carbon atoms or phenyl, which is unsubstituted or substituted by 1–2 substituents selected from the group consisting of F, Cl, CF$_3$, CH$_3$, methoxy and dimethylamino;

or

R(25) —is —(C$_1$–C$_9$)-heteroaryl, which is unsubstituted or substituted by 1–2 substituents selected from the group consisting of F, Cl, —CF$_3$, CH$_3$, methoxy and dimethylamino;

R(26) and R(27) independently of one another are hydrogen or alkyl having 1, 2, 3 or 4 carbon atoms;

R(4) is —CF$_3$, alkyl having 1, 2, 3, 4, 5 or 6 carbon atoms, alkenyl having 2, 3, 4, 5 or 6 carbon atoms, —(C$_5$–C$_6$)-cycloalkyl or —CH$_2$R(14);

R(14) is —(C$_5$–C$_6$)-cycloalkyl or phenyl, which is unsubstituted or substituted by 1–2 substituents selected from the group consisting of F and Cl, —CF$_3$, methyl and methoxy;

or

R(4) is phenyl, which is substituted by 2, 3, 4 or five substituents selected from the group consisting of F, Cl, CF$_3$, methyl and methoxy;

and their pharmaceutically tolerable salts.

Particularly preferred compounds of the formula I are those in which:

one of the radicals R(1), R(2), R(3) and R(5) is

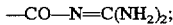
—CO—N=C(NH$_2$)$_2$;

and the other radicals R(1), R(2), R(3) and R(5) in each case are:

R(1) and R(5) independently of one another are hydrogen, alkyl having 1, 2, 3 or 4 carbon atoms, F, Cl, OH, methoxy or —CF$_3$;

R(2) is hydrogen, F, Cl, OH, —CF$_3$, alkyl having 1, 2, 3 or 4 carbon atoms, alkenyl having 2, 3 or 4 carbon atoms or —(CH$_2$)$_m$R(14);

m is zero, 1 or 2;

R(14) is —(C$_3$–C$_8$)-cycloalkyl or phenyl, which is unsubstituted or substituted by 1–2 substituents selected from the group consisting of F and Cl, —CF$_3$, methyl and methoxy;

or

R(2) is R(22)—SO$_2$—, R(23)R(24)N—CO—, R(28)—CO— or R(29)R(30)N—SO$_2$—;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen, methyl or ethyl;

or

R(35) and R(36) together are 4–5 methylene groups, of which a CH$_2$ group can be replaced by oxygen, —S—, —NH— or —NCH$_3$;

R(3) is hydrogen, —SR(25), —OR(25), —NR(25)R(26) or —CR(25)R(26)R(27);

R(25) is hydrogen, alkyl having 1, 2, 3 or 4 carbon atoms or phenyl, which is unsubstituted or substituted by 1–2 substituents selected from the group consisting of F, Cl, CF$_3$, CH$_3$, methoxy and dimethylamino;

or

R(25) is —(C$_1$–C$_9$)-heteroaryl, which is unsubstituted or substituted by 1–2 substituents selected from the group consisting of F, Cl, CF$_3$, CH$_3$, methoxy and dimethylamino;

R(26) and R(27) independently of one another are hydrogen or alkyl having 1, 2, 3 or 4 carbon atoms;

R(4) is CF$_3$, alkyl having 1, 2, 3, 4, 5 or 6 carbon atoms, alkenyl having 2, 3, 4, 5 or 6 carbon atoms, —(C$_5$–C$_6$)-cycloalkyl or —CH$_2$R(14);

R(14) is —(C$_5$–C$_6$)-cycloalkyl or phenyl, which is unsubstituted or substituted by 1–2 substituents selected from the group consisting of F and Cl, —CF$_3$, methyl and methoxy;

or

R(4) is phenyl, which is substituted by 2, 3, 4 or five substituents selected from the group consisting of F, Cl, CF$_3$, methyl and methoxy;

and their pharmaceutically tolerable salts.

Very particularly preferred compounds of the formula I are those in which:

one of the radicals R(1), R(2), R(3) and R(5) is

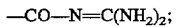
—CO—N=C(NH$_2$)$_2$;

and the other radicals R(1), R(2), R(3) and R(5) in each case are:

R(1) and R(5) independently of one another are hydrogen, alkyl having 1, 2, 3 or 4 carbon atoms, F, Cl, OH, methoxy or —CF$_3$;

R(2) is hydrogen, F, Cl, OH, —CF$_3$, alkyl having 1, 2, 3 or 4 carbon atoms or —(CH$_2$)$_m$R(14);

m is zero, 1 or 2;

R(14) is —(C$_5$–C$_6$)-cycloalkyl or phenyl, which is unsubstituted or substituted by 1–2 substituents selected from the group consisting of F and Cl, —CF$_3$, methyl and methoxy;

or

R(2) is —OR(35) or —NR(35)R(36);

R(35) and R(36) independently of one another are hydrogen, methyl or ethyl;

or

R(35) and R(36) together are 4–5 methylene groups, of which a CH$_2$ group can be replaced by oxygen, —S—, —NH— or —NCH$_3$;

R(3) is hydrogen or —OR(25);

R(25) is hydrogen, alkyl having 1, 2, 3 or 4 carbon atoms or phenyl, which is unsubstituted or substituted by 1–2 substituents selected from the group consisting of F, Cl, CF$_3$, CH$_3$ and methoxy;

or

R(25) is —(C$_1$–C$_9$)-heteroaryl, which is unsubstituted or substituted by 1–2 substituents from the group consisting of F, Cl, —CF$_3$, CH$_3$ and methoxy;

R(4) is CF$_3$, alkyl having 1, 2, 3, 4, 5 or 6 carbon atoms, alkenyl having 2, 3, 4, 5 or 6 carbon atoms, —(C$_5$–C$_6$)-cycloalkyl or —CH$_2$R(14);

R(14) is —(C$_5$–C$_6$)-cycloalkyl or phenyl, which is unsubstituted or substituted by 1–2 substituents from the group consisting of F, Cl, —CF$_3$, methyl and methoxy;

or

R(4) is phenyl, which is substituted by 2, 3, 4 or five substituents selected from the group consisting of F, Cl, CF$_3$, methyl and methoxy;

and their pharmaceutically tolerable salts.

The designated alkyl radicals can be straight-chain or branched.

(C$_1$–C$_9$)-Heteroaryl is understood as meaning radicals which are derived from phenyl or naphthyl, in which one or more CH groups are replaced by N and/or in which at least two adjacent CH groups (with formation of a five-membered aromatic ring) are replaced by S, NH or O. In addition, one or both atoms of the condensation site of bicyclic radicals (as in indolizinyl) can also be N atoms.

Heteroaryl is, in particular, furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl.

If one of the substituents R(1) to R(5) contains one or more centers of asymmetry, these can be present independently of one another in either the S or R configuration. The compounds can be present as optical isomers, as diastereomers, as racemates or as mixtures thereof.

The invention furthermore relates to a process for the preparation of the compounds I, which comprises reacting compounds of the formula II

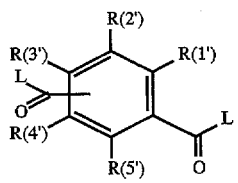

in which R(1') to R(5') have the meanings indicated above for R(1) to R(5), but of which at least one of the substituents R(1') to R(5') is the marked COL group, and in which L is a leaving group which can be easily nucleophilically substituted, with guanidine.

The activated acid derivatives of the formula II, in which L is an alkoxy group, preferably a methoxy group or phenoxy group, a phenylthio, methylthio or 2-pyridylthio group, or a nitrogen heterocycle, preferably 1-imidazolyl, are advantageously obtained in a manner known per se from the underlying carbonyl chlorides (formula II, L=Cl), which for their part can in turn be prepared in a manner known per se from the underlying carboxylic acids (formula II, L=OH), for example using thionyl chloride. In addition to the carbonyl chlorides of the formula II (L=Cl) further activated acid derivatives of the formula II can be prepared in a manner known per se directly from the underlying benzenedicarboxylic acid derivatives (formula II, L=OH), such as, for example, the methyl esters of the formula II where L=OCH$_3$ by treating with gaseous HCl in methanol, the imidazolides of the formula II by treating with carbonyldiimidazole [L=1-Imidazolyl, Staab, Angew. Chem. Int. Ed. Engl. 1,351–367 (1962)], the mixed anhydrides II with Cl—COOC$_2$H$_5$ or tosyl chloride in the presence of triethylamine in an inert solvent, and also the activation of benzenedicarboxylic acids using dicyclohexylcarbodiimide (DCC) or using O-[(cyano)ethoxycarbonyl)methylene) amino]-1,1,3,3-tetramethyluronium tetrafluoroborate] ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are indicated under details of source literature in J. March, Advanced Organic Chemistry, Third Edition (John Wiley & Sons, 1985), p. 350.

The reaction of an activated carboxylic acid derivative of the formula I with guanidine is carried out in a manner known per se in a protic or aprotic polar but inert organic solvent. In the case of the reaction of the methyl benzenedicarboxylates (II, L=OMe) with guanidine, methanol, isopropanol or THF between 20° C. and the boiling points of these solvents have proven suitable here. Most reactions of compounds II with salt-free guanidine were advantageously carried out in inert solvents such as THF, dimethoxyethane, dioxane or isopropanol. However, water can also be used as a solvent.

If L=Cl, the reaction is advantageously carried out with addition of an acid scavenger, e.g. in the form of excess guanidine to bind the hydrohalic acid. The introduction of the compounds substituted in the phenyl moiety by sulfur, oxygen or nitrogen nucleophiles is carried out by methods known from the literature for the nucleophilic substitution of derivatives of dialkyl benzenedicarboxylates. In this substitution, suitable leaving groups on the benzenedicarboxylic acid derivative have proven to be halides and trifluoromethanesulfonates. The reaction is advantageously carried out in a dipolar aprotic solvent, such as DMF or TMU, at a temperature from 0° C. up to the boiling point of the solvent, preferably from 80° C. up to the boiling point of the solvent. The acid scavenger used is advantageously an alkali metal or alkaline earth metal salt with an anion of high basicity and low nucleophilicity, for example K$_2$CO$_3$ or CsCO$_3$.

The alkyl or aryl substituents are introduced by methods known from the literature for the palladium-mediated crosscoupling of aryl halides with, for example, organozinc compounds, organostannanes, organoboronic acids or organoboranes.

In general, benzenedicarboxylic acid diguanides I are weak bases and can bind acid with formation of salts. Possible acid addition salts are salts of all pharmacologically tolerable acids, for example halides, in particular hydrochlorides, ascorbates, lactates, sulfates, citrates, tartrates, acetates, phosphates, methylsulfonates and p-toluenesulfonates.

U.S. Pat. No. 5,091,394 (HOE 89/F 288) and European Offenlegungsschrift 0 556 674 (HOE 92/F 034) describe benzoylguanidines, but not benzenedicarboxylic acid diguanides. WO 94/26709 discloses a benzoylguanidine which contains a nitrophenyl substituent in the 5-position. Polysubstituted 5-phenylbenzoylguanidines, however, are neither disclosed nor suggested there.

On account of their pharmacological properties, the compounds are outstandingly suitable as antiarrhythmic pharmaceuticals having a cardioprotective component for infarct prophylaxis and infarct treatment and for the treatment of angina pectoris, where they also preventively inhibit or greatly decrease the pathophysiological processes in the formation of ischemically induced damage, in particular in the induction of ischemically induced cardiac arrythmias. Because of their protective actions against pathological hypoxic and ischemic situations, the compounds of the formula I according to the invention can be used, as a result of inhibition of the cellular Na$^+$/H$^+$ exchange mechanism, as pharmaceuticals for the treatment of all acute or chronic damage caused by ischemia or illnesses primarily or secondarily induced thereby. This relates to their use as medicaments for surgical interventions, e.g. in organ transplantation, where the compounds can be used both for the protection of the organs in the donor before and during removal, for the protection of removed organs, for example during treatment with or storage thereof in physiological bath fluids, and also during transfer to the recipient's body. The compounds are also useful pharmaceuticals having a protective action when carrying out angioplastic surgical interventions, for example on the heart and also on peripheral vessels. In accordance with their protective action against ischemically induced damage, the compounds are also suitable as pharmaceuticals for the treatment of ischemias of the nervous system, in particular of the CNS, where they are suitable, for example, for the treatment of stroke or of cerebral edema. Moreover, the compounds of the formula I according to the invention are also suitable for the treatment of forms of shock, such as, for example, of allergic, cardiogenic, hypovolemic and bacterial shock.

The compounds of the formula I according to the invention are moreover distinguished by potent inhibitory action on the proliferation of cells, for example fibroblast cell proliferation and the proliferation of vascular smooth muscle cells. The compounds of the formula I are therefore suitable as useful therapeutics for illnesses in which cell proliferation is a primary or secondary cause, and can therefore be used as antiatherosclerotics, agents against diabetic late complications, carcinomatous disorders, fibrotic disorders such as pulmonary fibrosis, fibrosis of the liver or fibrosis of the kidney, organ hypertrophies and hyperplasias, in particular in prostate hyperplasia or prostate hypertrophy.

The compounds according to the invention are effective inhibitors of the cellular sodium-proton antiporter ($Na^+/H^+$ exchanger), which is raised in numerous disorders (essential hypertension, atherosclerosis, diabetes etc.) even in those cells which are easily accessible to measurement, such as, for example, in erythrocytes, platelets or leucocytes. The compounds according to the invention are therefore suitable as outstanding and simple scientific tools, for example in their use as diagnostics for the determination and differentiation of certain forms of hypertension, but also of atherosclerosis, diabetes, proliferative disorders etc. The compounds of the formula I are moreover suitable for preventive therapy for the prevention of the genesis of high blood pressure, for example; of essential hypertension.

Compared with most known compounds, the compounds according to the invention have a significantly improved water solubility. They are therefore significantly better suited to i.v. administration.

Compared with the known readily water-soluble compounds, the compounds according to the invention are distinguished by their better bioavailability and pharmacokinetics.

Pharmaceuticals which contain a compound I can be administered orally, parenterally, intravenously, rectally or by inhalation, the preferred type of administration being dependent on the particular clinical picture of the disorder. The compounds I can be used here on their own or together with pharmaceutical auxiliaries, for example in veterinary and also in human medicine.

On the basis of his expert knowledge, the person skilled in the art is familiar with which auxiliaries are suitable for the desired pharmaceutical formulation. Beside solvents, gelling agents, suppository bases, tablet auxiliaries and other active compound excipients, antioxidants, dispersants, emulsifiers, antifoams, flavor corrigents, preservatives, solubilizers or colorants, for example, can be used. For a form for oral administration, the active compounds are mixed with the additives suitable for this purpose, such as excipients, stabilizers or inert diluents and brought by the customary methods into the suitable administration forms, such as tablets, coated tablets, hard gelatin capsules, aqueous, alcoholic or oily solutions. Inert excipients which can be used are, for example, gum arabic, magnesia, magnesium carbonate, potassium phosphate, lactose, glucose or starch, in particular corn starch. Preparation can in this case take place either as dry or as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired with the substances customary for this purpose, such as solubilizers, emulsifiers or other auxiliaries. Possible solvents are, for example: water, physiological saline solution or alcohols, e.g. ethanol, propanol, glycerol, additionally also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation can also contain still other pharmaceutical auxiliaries such as surfactants, emulsifiers and stabilizers, as well as a propellant. Such a preparation customarily contains the active compound in a concentration from approximately 0.1 to 10, in particular from approximately 0.3 to 3% by weight.

The dose of the active compound of the formula I to be administered and the frequency of administration depend on the potency and duration of action of the compounds used; additionally also on the measure and severity of the illness to be treated and on the sex, age, weight and individual responsiveness of the mammal to be treated.

On average, the daily dose of a compound of the formula I in the case of a patient weighing approximately 75 kg is at least 0.001 mg/kg of body weight, preferably at least 0.01 mg/kg of body weight, up to at most 10 mg/kg of body weight, preferably to at most 1 mg/kg of body weight. In acute episodes of the illness, for example immediately after suffering a cardiac infarct, still higher and especially more frequent doses may also be necessary, e.g. up to 4 individual doses per day. In particular when administered i.v., for example in the case of an infarct patient in the intensive care unit, up to 100 mg per day may be necessary.

List of abbreviations:

Bn benzyl
Brine saturated aqueous NaCl solution
$CH_2Cl_2$ dichlormethane
DCI desorption chemical ionisation
DIP diisopropyl ether
DMA dimethylacetamide
DME dimethoxyethane
DMF N,N-dimethylformamide
EA ethyl acetate (EtOAc)
EI electron impact
eq equivalent
ES electrospray ionisation
Et ethyl
FAB fast atom bombardment
HEP n-heptane
HOAc acetic acid
Me methyl
MeOH methanol
mp melting point
MTB methyl tertiary-butyl ether
NBS N-bromosuccinimide
NMP N-methylpyrrolidone
RT room temperature
THF tetrahydrofuran
TMU N,N,N',N'-tetramethylurea
Tol toluene
CNS central nervous system
Experimental section
General procedure for the preparation of benzenedicarboxylic acid diguanides (I) from dialkyl benzenedicarboxylates (II, L=O-alkyl)
5 mmol of the dialkyl benzenedicarboxylate of the formula (II) and 50 mmol of guanidine (free base) are dissolved in 5 ml of isopropanol and boiled under reflux (typical reaction time 5 minutes to 5 h) until reaction is complete (thin-layer checking). The mixture is then diluted with 150 ml of water and the product is filtered off with suction. If appropriate, it is chromatographed on silica gel using a suitable eluent, e.g. EA/MeOH 5:1.

EXAMPLE 1

5-t-butylisophthalic acid diguanide

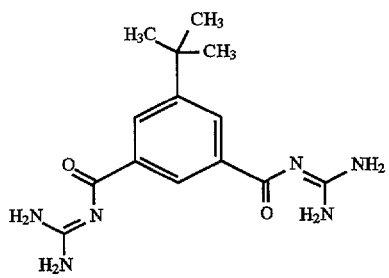

2.9 g of dimethyl-5-t-butylisophthalate are reacted (reaction time 10 minutes) according to the general procedure for the preparation of benzenedicarboxylic acid diguanides (I). 2.7 g of white crystals are obtained, mp>270° C. $R_f$ (acetone/water 10:1)=0.13 MS (ES): 305 (M+H)$^+$

EXAMPLE 2

5-[3,5-bis(trifluoromethyl)phenyl]isophthalic acid diguanide

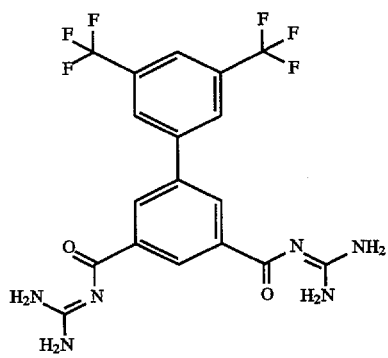

600 mg of dimethyl 5-[3,5-bis(trifluoromethyl)phenyl] isophthalate are reacted (reaction time 10 minutes) according to the general procedure for the preparation of benzene-dicarboxylic acid diguanides (I). 580 mg of white crystals are obtained, mp 248° C. with decomposition. $R_f$ (acetone/water 10:1)=0.21 MS (FAB): 461 (M+H)$^+$ 2 a: Dimethyl 5-[3,5-bis(trifluoromethyl)phenyl] isophthalate 3.73 g of dimethyl 5-bromoisophthalate, 2.74 g of 3,5-bis(trifluoromethyl)phenylboronic acid, 2.1 g of Na$_2$CO$_3$, 225 mg of Pd(II) acetate and 525 mg of triphenylphosphine are stirred at 100° C. for 3 h in 100 ml of toluene and 20 ml of water. The mixture is allowed to cool, and is diluted with 200 ml of EA and extracted twice with 100 ml of saturated aqueous NaHCO$_3$ solution each time. The organic phase is dried over Na$_2$SO$_4$ and the solvent is removed in vacuo. Chromatography on silica gel using EA/HEP 1:8 yields 1.3 g of a pale yellow solid, mp 151° C. $R_f$ (EA/HEP 1:8)=0.21 MS (FAB): 407 (M+H)$^+$ The title compounds of Examples 3–5 are synthesized analogously to Example 2, and the dimethyl ester precursors are obtained analogously to 2 a.

EXAMPLE 3

5-(3,5-dichlorophenyl)isophthalic acid diguanide

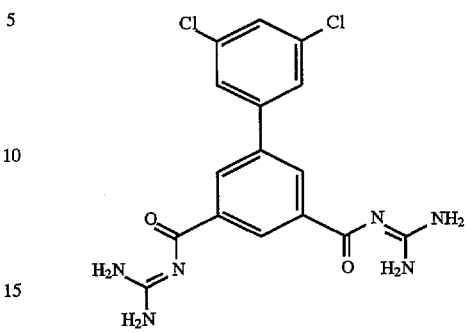

mp 250° C. with decomposition $R_f$ (acetone/water 10:1)= 0.13 MS (ES): 393 (M+H)$^+$

EXAMPLE 4

5-(2,4-dichlorophenyl)isophthalic acid diguanide

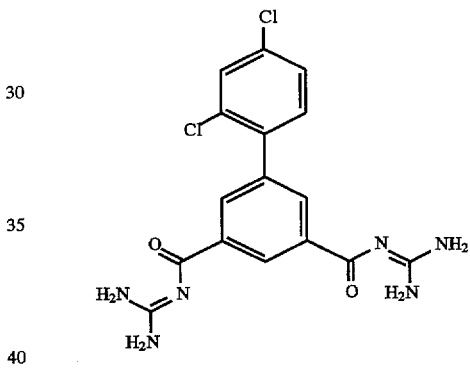

mp>250° C. with decomposition $R_f$ (acetone/water 10:1)= 0.15 MS (ES): 393 (M+H)$^+$

EXAMPLE 5

5-(3-chloro-4-fluorophenyl)isophthalic acid diguanide

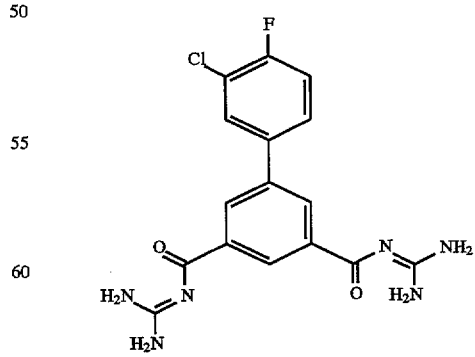

mp 231° C. with decomposition $R_f$ (acetone/water 10:1)= 0.14 MS (ES): 377 (M+H)$^+$

EXAMPLE 6
5-cyclohexylisophthalic acid diguanide

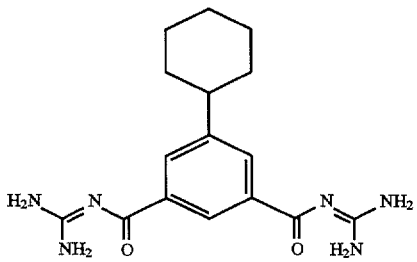

a) Dimethyl 5-cyclohexylisophthalate 22 ml of a 2M solution of cyclohexylmagnesium chloride in diethyl ether are added dropwise to 100 ml of a solution of 0.5M $ZnCl_2$ solution in THF. The mixture is stirred at 50° C. for 5 h and the organozinc compound is directly reacted further as solution A.

3.9 g of dimethyl isophthalate, 420 mg of [1,1-bis (diphenylphosphino)ferrocene]Pd(II) chloride and 130 mg of CuI are suspended in 70 ml of THF. Solution A is then added dropwise at RT and stirred at this temperature for 8 h. The reaction mixture is poured onto 300 ml of saturated aqueous $NaHCO_3$ solution, diluted with 100 ml of water, and the precipitate is filtered off and extracted 4 times with 200 ml of EA each time. The organic phase is dried over $Na_2SO_4$ and the solvent is removed in vacuo. Chromatography on silica gel using EA/HP 1:4 yields 2.7 g of a colorless oil. $R_f$ (EA/HEP 1:4)=0.40 MS (FAB): 277 $(M+H)^+$ b) 5-Cyclohexylisophthalic acid diguanide 5.3 g of guanidine hydrochloride are dissolved in 55 ml of DMF and a solution of 5.6 g of potassium tert-butoxide dissolved in 50 ml of DMF is added dropwise at RT. The mixture is subsequently stirred at RT for 2 h, then a solution of 1.4 g of dimethyl 5-cyclohexylisophthalate in 15 ml of DMF is added dropwise and stirred at RT for 24 h. The reaction mixture is poured onto 1 l of water and extracted 3 times with 100 ml of EA each time. The organic phase is dried over $Na_2SO_4$ and the solvent is removed in vacuo. The residue is suspended in 50 ml of EA and adjusted to pH=2–3 using a saturated solution of maleic acid in EA. The crystalline residue is filtered off, washed with 50 ml of EA and subsequently dissolved in 50 ml each of a saturated aqueous $Na_2CO_3$ solution, a saturated aqueous $NaHCO_3$ solution and water and the free base is isolated by extraction 3 times with 100 ml of EA each time. The organic phase is dried over $Na_2SO_4$ and the solvent is removed in vacuo. 1.1 g of colorless crystals are obtained, mp 219°–220° C. $R_f$ (acetone/water 10:1)=0.23 MS (FAB): 331 $(M+H)^+$ Pharmacological data:

Inhibition of the $Na^+/H^+$ exchanger of rabbit erythrocytes White New Zealand rabbits (Ivanovas) received a standard diet with 2% cholesterol for six weeks in order to activate $Na^+/H^+$ exchange and thus to be able to determine the $Na^+$ influx into the erythrocytes via $Na^+/H^+$ exchange by flame photometry. The blood was taken from the ear arteries and rendered incoagulable by means of 25 IU of potassium heparin. A part of each sample was used for the duplicate determination of the haematocrit by centrifugation. Aliquots of 100 µl in each case were used to measure the $Na^+$ starting content of the erythrocytes.

In order to determine the amiloride-sensitive sodium influx, 100 µl of each blood sample were incubated in each case in 5 ml of a hyperosmolar salt-sucrose medium (mmol/l: 140 NaCl, 3 KCl, 150 sucrose, 0.1 ouabain, 20 trishydroxymethylaminomethane) at pH 7.4 and 37° C. The erythrocytes were then washed three times with ice-cold $MgCl_2$ ouabain solution (mmol/l: 112 $MgCl_2$, 0.1 ouabain) and hemolyzed in 2.0 ml of distilled water. The intracellular sodium content was determined by flame photometry.

The net $Na^+$ influx was calculated from the difference between sodium starting values and the sodium content of the erythrocytes after incubation. The amiloride-inhibitable sodium influx resulted from the difference between the sodium content of the erythrocytes after incubation with and without amiloride $3 \times 10^{-4}$ mol/l. This procedure was also used in the case of the compounds according to the invention.

Results

Inhibition of the $Na^+/H^+$ exchanger:

| Example | $IC_{50}$ mol/l |
| --- | --- |
| 1 | 0.15 |
| 3 | 0.2 |
| 5 | 0.2 |

What is claimed is:

1. A benzenedicarboxylic acid diguanide of the formula I

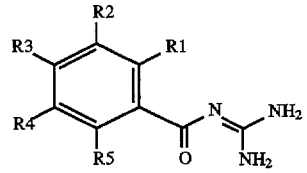

in which:

one of the radicals R(1), R(2), R(3) and R(5) is

—CO—N=C(NH$_2$)$_2$;

and the other radicals R(1), R(2), R(3) and R(5) in each case are:

R(1) and R(5) independently of one another are hydrogen, alkyl having 1, 2, 3 or 4 carbon atoms, F, Cl, —OR(32), —NR(33)R(34) or CF$_3$;

R(32), R(33) and R(34) independently of one another are hydrogen or alkyl having 1, 2, 3 or 4 carbon atoms;

R(2) is hydrogen, F, Cl, Br, I, OH, —CN, CF$_3$, —CO—N=C(NH$_2$)$_2$, alkyl having 1, 2, 3, 4, 5, 6, 7 or 8 carbon atoms, alkenyl having 2, 3, 4, 5, 6, 7 or 8 carbon atoms or —(CH$_2$)$_m$R(14);

m is zero, 1 or 2;

R(14) is —(C$_3$–C$_8$)-cycloalkyl or phenyl, which is unsubstituted or substituted by 1–3 substituents selected from the group consisting of F and Cl, —CF$_3$, methyl, methoxy and —NR(15)R(16);

R(15) and R(16) are hydrogen or —CH$_3$;

or

R(2) is R(22)—SO$_2$—, R(23)R(24)N—CO—, R(28)—CO— or R(29)R(30)N—SO$_2$—;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen or alkyl having 1, 2, 3, 4, 5 or 6 carbon atoms;

or

R(35) and R(36) together are 4–7 methylene groups, of which a CH$_2$ group can be replaced by oxygen, —S—, —NH—, —NCH$_3$ or —N-benzyl;

R(3) is hydrogen, —SR(25), —OR(25), —NR(25)R(26), —CR(25)R(26)R(27);

R(25) is hydrogen, alkyl having 1, 2, 3, 4, 5, 6, 7 or 8 carbon atoms or phenyl, which is unsubstituted or substituted by 1–3 substituents selected from the group consisting of F, Cl, CF$_3$, CH$_3$, methoxy, hydroxyl, amino, methylamino and dimethylamino;

or

R(25) is —(C$_1$–C$_9$)-heteroaryl, which is unsubstituted or substituted by 1–3 substituents selected from the group consisting of F, Cl, CF$_3$, CH$_3$, methoxy, hydroxyl, amino, methylamino and dimethylamino;

R(26) and R(27) independently of one another are defined as R(25) or are hydrogen or alkyl having 1, 2, 3, 4, 5, 6, 7 or 8 carbon atoms;

R(4) is CF$_3$, alkyl having 1, 2, 3, 4, 5, 6, 7 or 8 carbon atoms, alkenyl having 2, 3, 4, 5, 6, 7 or 8 carbon atoms, —(C$_3$–C$_8$)-cycloalkyl or —(CH$_2$)$_m$R(14);

m is 1 or 2;

R(14) —is —(C$_3$–C$_8$)-cycloalkyl or phenyl, which is unsubstituted or substituted by 1–3 substituents selected from the group consisting of F and Cl, —CF$_3$, methyl, methoxy and —NR(15)R(16);

R(15) and R(16) are hydrogen or —CH$_3$;

or

R(4) is phenyl, which is substituted by 2, 3, 4 or five substituents selected from the group consisting of F, Cl, CF$_3$, methyl, methoxy and —NR(15)R(16);

R(15) and R(16) independently of one another are hydrogen or CH$_3$;

or its pharmaceutically tolerable salts.

2. A compound of the formula I as claimed in claim 1 in which:

one of the radicals R(1), R(2), R(3) and R(5) is

—CO—N=C(NH$_2$)$_2$;

and the other radicals R(1), R(2), R(3) and R(5) in each case are

R(1) and R(5) independently of one another are hydrogen, alkyl having 1, 2, 3 or 4 carbon atoms, F, Cl, —OR(32) or —CF$_3$;

R(32) is hydrogen or alkyl having 1, 2, 3 or 4 carbon atoms;

R(2) is hydrogen, F, Cl, Br, I, OH, CF$_3$, alkyl having 1, 2, 3 or 4 carbon atoms, alkenyl having 2, 3 or 4 carbon atoms or —(CH$_2$)$_m$R(14);

m is zero, 1 or 2;

R(14) is —(C$_3$–C$_8$)-cycloalkyl or phenyl, which is unsubstituted or substituted by 1–2 substituents selected from the group consisting of F and Cl, —CF$_3$, methyl and methoxy;

or

R(2) is R(22)—SO$_2$—, R(23)R(24)N—CO—, R(28)—CO— or R(29)R(30)N—SO$_2$—;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen, methyl or ethyl;

or

R(35) and R(36) together are 4–5 methylene groups, of which a CH$_2$ group can be replaced by oxygen, —S—, —NH— or —NCH$_3$;

R(3) is hydrogen, —SR(25), —OR(25), —NR(25)R(26) or —CR(25)R(26)R(27);

R(25) is hydrogen, alkyl having 1, 2, 3 or 4 carbon atoms or phenyl, which is unsubstituted or substituted by 1–2 substituents selected from the group consisting of F, Cl, CF$_3$, CH$_3$, methoxy and dimethylamino;

or

R(25) —is —(C$_1$–C$_9$)-heteroaryl, which is unsubstituted or substituted by 1–2 substituents selected from the group consisting of F, Cl, —CF$_3$, CH$_3$, methoxy and dimethylamino;

R(26) and R(27) independently of one another are hydrogen or alkyl having 1, 2, 3 or 4 carbon atoms;

R(4) is —CF$_3$, alkyl having 1, 2, 3, 4, 5 or 6 carbon atoms, alkenyl having 2, 3, 4, 5 or 6 carbon atoms, —(C$_5$–C$_6$)-cycloalkyl or —CH$_2$R(14);

R(14) is —(C$_5$–C$_6$)-cycloalkyl or phenyl, which is unsubstituted or substituted by 1–2 substituents selected from the group consisting of F and Cl, —CF$_3$, methyl and methoxy;

or

R(4) is phenyl, which is substituted by 2, 3, 4 or five substituents selected from the group consisting of F, Cl, CF$_3$, methyl and methoxy;

or its pharmaceutically tolerable salts.

3. A compound of the formula I as claimed in claim 1, wherein:

one of the radicals R(1), R(2), R(3) and R(5) is

—CO—N=C(NH$_2$)$_2$;

and the other radicals R(1), R(2), R(3) and R(5) in each case are:

R(1) and R(5) independently of one another hydrogen, alkyl having 1, 2, 3 or 4 carbon atoms, F, Cl, OH, methoxy or —CF$_3$;

R(2) is hydrogen, F, Cl, OH, —CF$_3$, alkyl having 1, 2, 3 or 4 carbon atoms, alkenyl having 2, 3 or 4 carbon atoms or —(CH$_2$)$_m$R(14);

m is zero, 1 or 2;

R(14) is —(C$_3$–C$_8$)-cycloalkyl or phenyl, which is unsubstituted or substituted by 1–2 substituents selected from the group consisting of F and Cl, —CF$_3$, methyl and methoxy;

or

R(2) is R(22)—SO$_2$—, R(23)R(24)N—CO—, R(28)—CO— or R(29)R(30)N—SO$_2$—;

R(22) and R(28) independently of one another are methyl or —CF$_3$;

R(23), R(24), R(29) and R(30) independently of one another are hydrogen or methyl;

or

R(2) is —OR(35) or —NR(35)R(36);

R(35) and R(36) independently of one another are hydrogen, methyl or ethyl;

or

R(35) and R(36) together are 4–5 methylene groups, of which a CH$_2$ group can be replaced by oxygen, —S—, —NH— or —NCH$_3$;

R(3) is hydrogen, —SR(25), —OR(25), —NR(25)R(26) or —CR(25)R(26)R(27);

R(25) is hydrogen, alkyl having 1, 2, 3 or 4 carbon atoms or phenyl, which is unsubstituted or substituted by 1–2 substituents selected from the group consisting of F, Cl, $CF_3$, $CH_3$, methoxy and dimethylamino;

or

R(25) is —$(C_1-C_9)$-heteroaryl, which is unsubstituted or substituted by 1–2 substituents selected from the group consisting of F, Cl, $CF_3$, $CH_3$, methoxy and dimethylamino;

R(26) and R(27) independently of one another are hydrogen or alkyl having 1, 2, 3 or 4 carbon atoms;

R(4) is $CF_3$, alkyl having 1, 2, 3, 4, 5 or 6 carbon atoms, alkenyl having 2, 3, 4, 5 or 6 carbon atoms, —$(C_5-C_6)$-cycloalkyl or —$CH_2R(14)$;

R(14) is —$(C_5-C_6)$-cycloalkyl or phenyl, which is unsubstituted or substituted by 1–2 substituents selected from the group consisting of F and Cl, —$CF_3$, methyl and methoxy;

or

R(4) is phenyl, which is substituted by 2, 3, 4 or five substituents selected from the group consisting of F, Cl, $CF_3$, methyl and methoxy.

4. A compound of the formula I as claimed in claims 1, in which:

one of the radicals R(1), R(2), R(3) and R(5) is

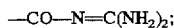

—CO—N=C(NH$_2$)$_2$;

and the other radicals R(1), R(2), R(3) and R(5) in each case are:

R(1) and R(5) independently of one another are hydrogen, alkyl having 1, 2, 3 or 4 carbon atoms, F, Cl, OH, methoxy or —$CF_3$;

R(2) is hydrogen, F, Cl, OH, —$CF_3$, alkyl having 1, 2, 3 or 4 carbon atoms or —$(CH_2)_mR(14)$;

m is zero, 1 or 2;

R(14) is —$(C_5-C_6)$-cycloalkyl or phenyl, which is unsubstituted or substituted by 1–2 substituents selected from the group consisting of F and Cl, —$CF_3$, methyl and methoxy;

or

R(2) is —OR(35) or —NR(35)R(36);

R(35) and R(36) independently of one another are hydrogen, methyl or ethyl;

or

R(35) and R(36) together are 4–5 methylene groups, of which a $CH_2$ group can be replaced by oxygen, —S—, —NH— or —$NCH_3$;

R(3) is hydrogen or —OR(25);

R(25) is hydrogen, alkyl having 1, 2, 3 or 4 carbon atoms or phenyl, which is unsubstituted or substituted by 1–2 substituents selected from the group consisting of F, Cl, $CF_3$, $CH_3$ and methoxy;

or

R(25) is —$(C_1-C_9)$-heteroaryl, which is unsubstituted or substituted by 1–2 substituents from the group consisting of F, Cl, —$CF_3$, $CH_3$ and methoxy;

R(4) is $CF_3$, alkyl having 1, 2, 3, 4, 5 or 6 carbon atoms, alkenyl having 2, 3, 4, 5 or 6 carbon atoms, —$(C_5-C_6)$-cycloalkyl or —$CH_2R(14)$;

R(14) is —$(C_5-C_6)$-cycloalkyl or phenyl, which is unsubstituted or substituted by 1–2 substituents from the group consisting of F, Cl, —$CF_3$, methyl and methoxy;

or

R(4) is phenyl, which is substituted by 2, 3, 4 or five substituents selected from the group consisting of F, Cl, $CF_3$, methyl and methoxy.

5. A compound I as claimed in claim 1, selected from the group comprising 5-t-butylisophthalic acid diguanide; 5-[3,5-bis(trifluoromethyl)phenyl]isophthalic acid diguanide; 5-(3,5-dichlorophenyl)isophthalic acid diguanide; 5-(2,4-dichlorophenyl)isophthalic acid diguanide; 5-(3-chloro-4-fluorophenyl)isophthalic acid diguanide; and 5-cyclohexylisophthalic acid diguanide.

6. A pharmaceutical composition comprising an effective amount for use as a pharmaceutical of a compound of the formula I as claimed in claim 1 together with a pharmaceutically acceptable carrier.

7. A method for the treatment or prophylaxis of illnesses caused by ischemic conditions which comprises administering to a mammal in need of such treatment or prophylaxis a pharmaceutical composition as set forth in claim 6.

8. A method for the treatment or prophylaxis of illnesses caused by ischemic conditions which comprises administering to a mammal in need of such treatment or prophylaxis an effective amount of a compound I as set forth in claim 1.

9. A method for the treatment or prophylaxis of cardiac infarct and of arrhythmias which comprises administerting to a mammal in need of such treatment or prophylaxis a pharmaceutical composition as set forth in claim 6.

10. A method for the treatment or prophylaxis of cardiac infarct and of arrhythmias which comprises administering to a mammal in need of such treatment or prophylaxis an effective amount of a compound I as set forth in claim 1.

11. A method for the treatment or prophylaxis of angina pectoris which comprises administering to a mammal in need of such treatment or prophylaxis a pharmaceutical composition as set forth in claim 6.

12. A method for the treatment or prophylaxis of angina pectoris which comprises administering to a mammal in need of such treatment or prophylaxis an effective amount of a compound I as set forth in claim 1.

13. A method for the treatment or prophylaxis of ischemic conditions of the heart comprising administering to a mammal in need of such treatment or prophylaxis a pharmaceutical composition as set forth in claim 6.

14. A method for the treatment or prophylaxis of ischemic conditions of the heart comprising administering to a mammal in need of such treatment or prophylaxis an effective amount of a compound I as set forth in claim 1.

15. A method for the treatment or prophylaxis of ischemic conditions of the peripheral and central nervous system and of stroke comprising administering to a mammal in need of such treatment or prophylaxis a pharmeutical composition as set forth in claim 6.

16. A method for the treatment or prophylaxis of ischemic conditions of the peripheral and central nervous system and of stroke comprising administering to a mammal in need of such treatment or prophylaxis an effective amount of a compound I as set forth in claim 1.

17. A method for the treatment or prophylaxis of ischemic conditions of the peripheral organs and members comprising administering to a mammal in need of such treatment or prophylaxis a pharmaceutical composition as set forth in claim 6.

18. A method for the treatment or prophylaxis of ischemic conditions of the peripheral organs and members comprising admininstering to a mammal in need of such treatment or prophylaxis an effective amount of a compound I as set forth in claim 1.

19. A method for the treatment of states of shock comprising administering to a mammal in need of such treatment a pharmaceutical composition as set forth in claim 6.

20. A method for the treatment of states of shock comprising administering to a mammal in need of such treatment an effective amount of a compound I as set forth in claim 1.

* * * * *